United States Patent [19]

Miller

[11] Patent Number: 4,612,937

[45] Date of Patent: Sep. 23, 1986

[54] ULTRASOUND DIAGNOSTIC APPARATUS

[75] Inventor: Lawrence R. Miller, Sacramento, Calif.

[73] Assignee: Siemens Medical Laboratories, Inc., Walnut Creek, Calif.

[21] Appl. No.: 809,363

[22] Filed: Dec. 16, 1985

[51] Int. Cl.$^4$ .............................................. A61B 10/00
[52] U.S. Cl. .................................... 128/663; 128/660; 73/861.25
[58] Field of Search ........................ 128/660, 661, 663; 73/861.25

[56] References Cited

U.S. PATENT DOCUMENTS

| | | | |
|---|---|---|---|
| 3,922,911 | 12/1975 | Groves et al. | 128/663 |
| 4,141,347 | 2/1979 | Green et al. | 128/663 |
| 4,205,687 | 6/1980 | White et al. | 128/663 |
| 4,217,909 | 8/1980 | Papadofrangakis et al. | 128/663 |
| 4,318,413 | 3/1982 | Iinuma et al. | 128/663 |
| 4,324,258 | 4/1982 | Huebscher et al. | 128/663 |
| 4,344,327 | 8/1982 | Yoshikawa et al. | 128/661 |
| 4,373,533 | 2/1983 | Iinuma | 128/663 |
| 4,416,286 | 11/1983 | Iinuma et al. | 128/663 |
| 4,476,874 | 10/1984 | Taenzer et al. | 128/663 |

OTHER PUBLICATIONS

Arenson et al., "A Linear Stepped Doppler Ultrasound Array for Real-Time Two Dimensional Blood Flow Imaging", 1980 Ultrasonics Symposium Proceedings Boston, Ma. (Nov. 5-7, 1980) pp. 775-779.

Primary Examiner—Kyle L. Howell
Assistant Examiner—Ruth S. Smith
Attorney, Agent, or Firm—Mark H. Jay

[57] ABSTRACT

An ultrasound diagnostic apparatus for displaying two-dimensional blood flow information superimposed over anatomical information. A transducer generates a series of ultrasound bursts which are directed towards the area of the body where blood flow and anatomical information are desired. The bursts are transmitted in several beam directions so as to form a sector scan. A receive interval follows each burst at which time the transducer detects ultrasound reflected from body structure and blood. A detector circuit receives the reflected ultrasound signals and produces a frequency difference signal which corresponds to the difference in frequency between the transmitted and reflected ultrasound, such difference being attributable to the Doppler shift produced by moving blood cells. The detected difference frequency data are forwarded to a processor unit which generates velocity estimator data for various points along each of the beam directions. The velocity estimator data are then used to produce an image of blood flow on a display, such as a television monitor. Preferably, blood flow toward and away from the transducer will appear in different colors. Anatomical data produced from the reflected ultrasound is also used to provide an image of the display of body structure with the anatomical image being superimposed over the blood flow image.

9 Claims, 9 Drawing Figures

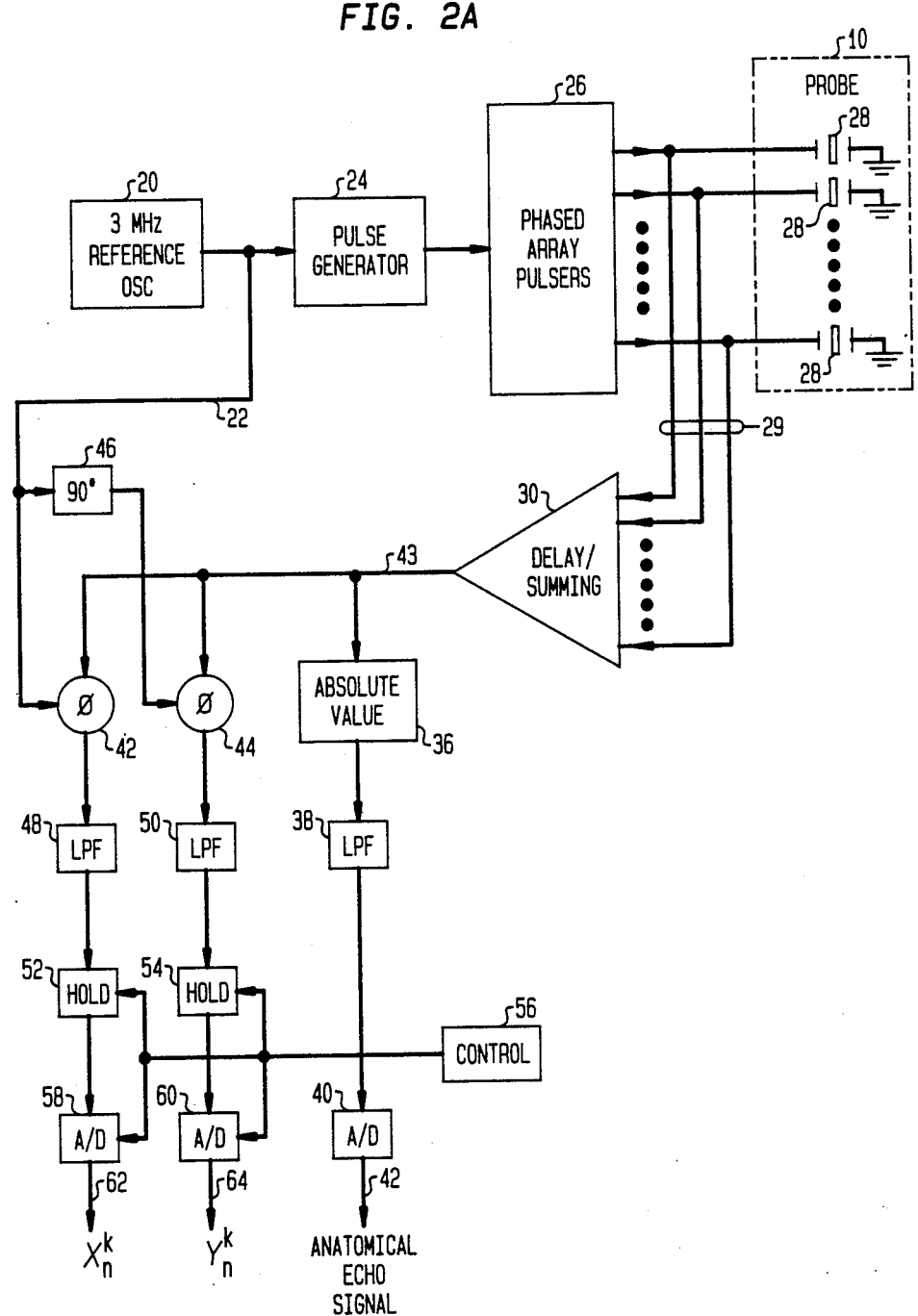

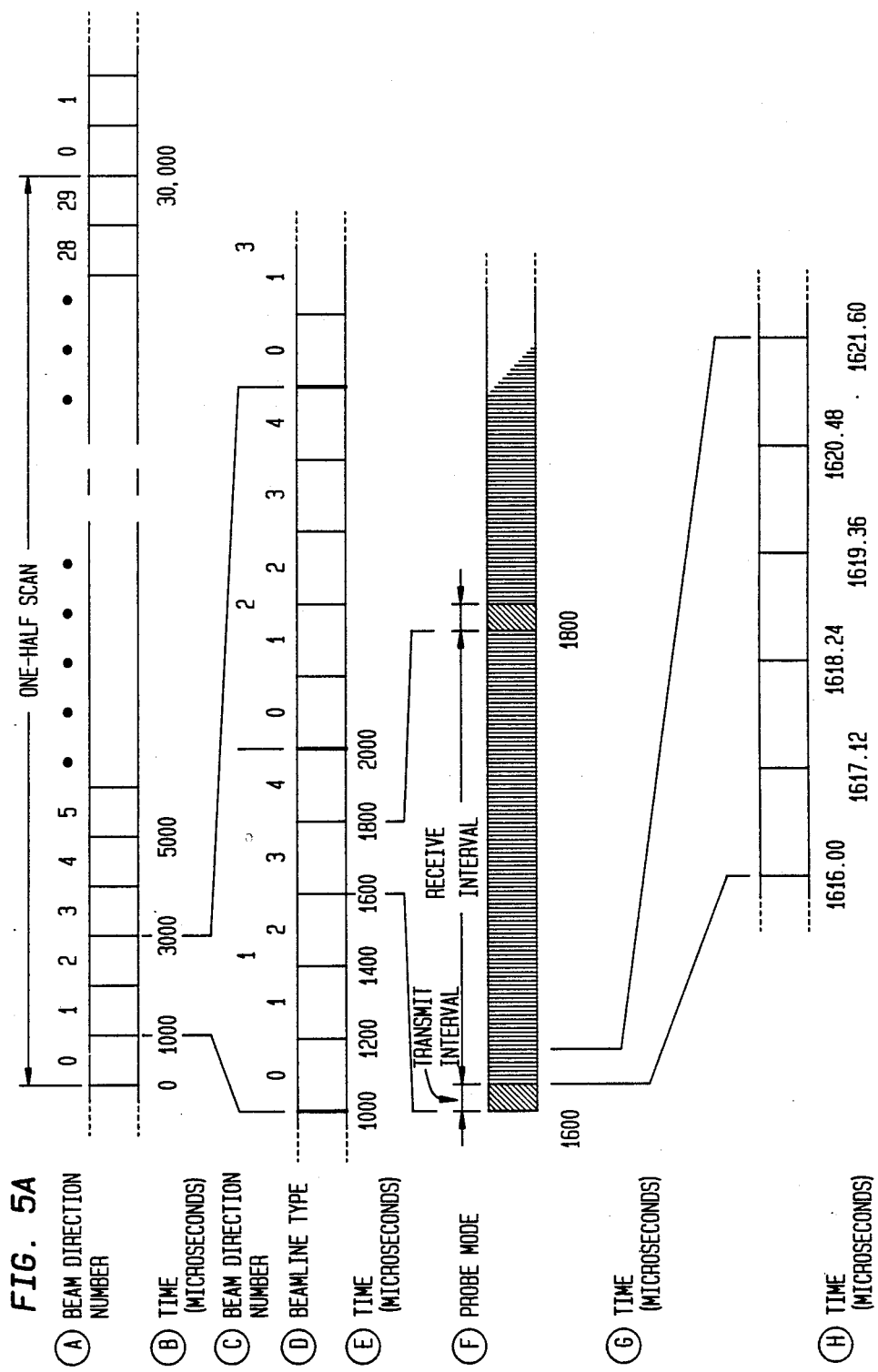

ULTRASOUND DIAGNOSTIC APPARATUS

TECHNICAL FIELD

The present invention relates generally to ultrasonic diagnostic apparatus and more particularly to apparatus which is capable of displaying superimposed anatomical and blood flow velocity information.

BACKGROUND ART

Diagnostic ultrasound apparatus provides a comprehensive evaluation of body health and disease. The proven safety and efficacy of ultrasound techniques have resulted in widespread acceptance by both patients and physicians.

Diagnostic ultrasound equipment generates images of structures within the body by transmitting ultrahigh frequency sound waves (typically on the order of 3.0 MHz) and then analyzing the waves reflected from the body structure. Perhaps the most widely used ultrasonic diagnostic apparatus displays structural information of an organ in the form of a two-dimensional image of a selected cross-section of the organ. The ultrasound is typically swept across the organ in the form of a sector scan. The sector scan is ordinarily performed in real time so that the image is available during the examination. In such cases, motion of the organ produces a corresonding moving image.

In cardiology, most diseases are accompanied by both anatomical and blood flow abnormalities. Although two-dimensional anatomical images have proved very useful in detecting, for example, mitral stenosis, intracardiac shunts and wall-motion abnormalities, it has been less useful in evaluating aortic stenosis, mitral and aortic insufficiency and congenital defects. In these latter areas, the anatomical defects are extremely small, and often beyond the resolution of conventional anatomical ultrasonic apparatus. However, flow abnormalities created by these defects are much more significant. Thus, if blood flow can be monitored, these abnormalities can be more easily detected.

Some presently-available ultrasound systems provide blood flow information utilizing the Doppler principle. Exemplary Doppler ultrasound apparatus are disclosed in U.S. Pat. No. 4,318,413 to Iinuma et al. and U.S. Pat. No. 4,324,258 to Heubscher et al. A beam of ultrasonic energy is directed toward a blood vessel or other organ in which blood flow information is desired. The moving blood cells reflect the ultrasound energy and either impart an increase or decrease in frequency to the reflected energy, depending on the direction of blood flow, in accordance with the Doppler principle. The magnitude of the frequency shift and direction of shift are detected so that the velocity and direction of blood flow may be ascertained. Such Doppler ultrasound apparatus also typically provide anatomical information using conventional diagnostic ultrasound techniques.

The Doppler ultrasound equipment now in use is deficient in many respects. Perhaps the most serious deficiency is that such equipment is capable of providing blood flow information at only one point or at several individual points in an organ. Since blood flow is frequently not uniform within an organ, even within a relatively small volume, it is difficult to obtain complete blood flow information using such equipment.

The present invention overcomes the above-noted limitations of Doppler ultrasound equipment. The disclosed ultrasonic diagnostic apparatus provides a real-time, two-dimensional blood flow image superimposed on a real-time, two-dimensional anatomical image. Blood flow information is displayed over the entire cross-section or a substantial portion of the cross-section of the organ rather than at a single point or multiple points. Thus, the examiner is able to ascertain blood flow information over an entire organ cross-section or a portion thereof at essentially a single point in time. This and other advantages of the present invention will become apparent to persons having ordinary skill in the art upon reading the following Best Mode for Carrying Out the Invention together with the drawings.

DISCLOSURE OF THE INVENTION

An ultrasound diagnostic apparatus for displaying two-dimensional blood flow information is disclosed. The apparatus includes a transducer array for transmitting a series of ultrasound bursts toward the area of the patient from which blood flow information is desired. The ultrasound is transmitted in a plurality of directions along a given plane, typically 64 different directions, so as to achieve a sector scan.

Ultrasound reflected from the blood is received by the transducer array and converted to corresponding electrical signals. Reflected ultrasound is periodically sampled during a receive interval following each transmitted burst of ultrasound. The sampled reflected ultrasound signals are fed to a detector circuit which detects a frequency difference between the transmitted and received ultrasound. The output of the detector circuit preferably includes in-phase and quadrature phase components.

A processor unit receives frequency difference data from the detector circuit and generates velocity estimator signals in response to such data. Each estimator signal is indicative of blood flow velocity at a predetermined one of a plurality of points along each beam direction. There are typically on the order of 174 of such points along each beam line. Preferably, each velocity estimator signal is produced from detected data from five bursts of transmitted ultrasound, although data from fewer or greater numbers of bursts may be acceptable.

The estimator signals are then coupled to a display such as a color television monitor. It is preferred that a scan converter memory be used to convert the format of the velocity estimator data from sector scan to standard raster scan. The display typically produces an image of blood flow away from the transducer array in one color, such as red, and another color, such as blue, for blood flow toward the transducer array. The brightness of the color is adjusted in accordance with the magnitude of the blood flow velocity.

BRIEF DESCRIPTION OF THE DRAWINGS

FIGS. 2A and 2B depict a block diagram of the subject ultrasound diagnostic apparatus.

FIGS. 5A and 5B are timing diagrams which depict exemplary memory read/write sequences of the processor unit.

BEST MODE FOR CARRYING OUT THE INVENTION

Figure 1:
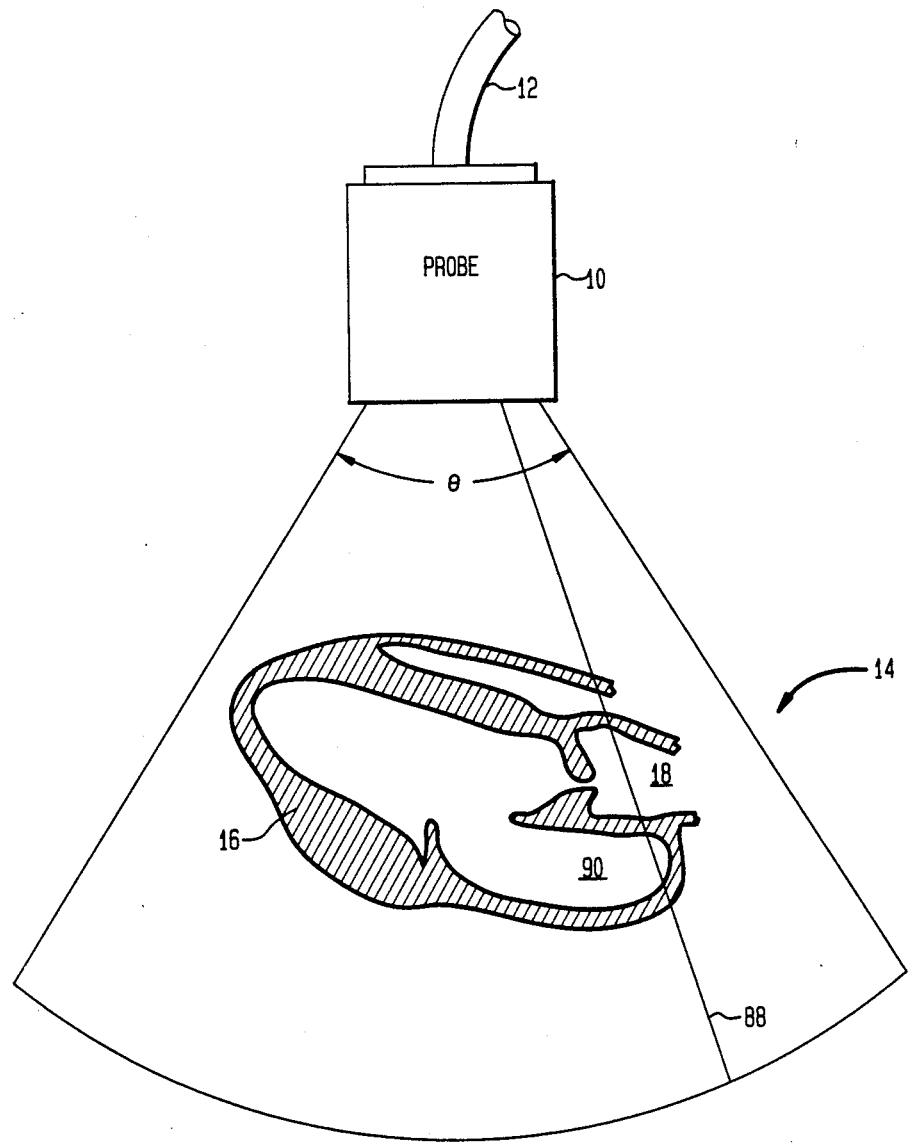
FIG. 1 is a diagram of an exemplary image produced by the subject ultrasound diagnostic apparatus and shows the corresponding position of the ultrasound transmitter/receiver probe which produced the image.

Referring now to FIG. 1 of the drawings, the subject ultrasound diagnostic apparatus includes a conventional phased array ultrasonic probe 10 connected to the main unit of the diagnostic equipment (not shown) by way of a multiwire cable 12. Probe 10 includes an array of piezoelectric transducers, as will be subsequently described, which are energized by electric excitation pulses in an approximately linear time sequence to form an ultrasound beam. A time delay is successively added to each excitation pulse so as to steer the ultrasound beam over a sector having a scan angle $\phi$ typically ranging from 60° to 90°. An additional small delay is added to the center elements, primarily in order to focus the beam, as is well known. Ultrasound reflections or echoes returning from a given target in the direction of the transmitted beam arrive at the transducer elements at different times. Thus, additional time delay circuitry is provided in the receiving portion of the equipment so that all the signals produced by reflections from a given point in the body are summed simultaneously.

The sector scan image, generally designated by the numeral 14, is displayed on the color CRT of a television monitor. Image 14 is formed by performing a transmit/receive sequence along successive beam lines. One such beam line is depicted in FIG. 1 as line 88. As will subsequently be described in greater detail, the image data are acquired as ultrasound beams are sequentially produced throughout the sector over angle $\phi$, and are stored in a scan converter memory. The data are then read out of the scan converter memory in order to produce the television image 14 ued a standard raster scan format.

Image 14 is produced from typically $5 \times 64 = 320$ bursts of ultrasound at various directions through angle $\phi$. Each burst has a duration of about 8 microseconds. The frequency of the ultrasound is on the order of 3 MHz, although somewhat higher frequencies can be used to achieve greater resolution and lower frequencies can be used to achieve greater penetration.

The ultrasound bursts are spaced typically approximately 200 microseconds from one another. During the approximately 190 microsecond period between bursts, probe 10 acts as a receiver. Returning ultrasound reflected from body structure and groups of red blood cells are sampled approximately once every 1.12 microseconds for use by the blood flow processing circuitry and approximately once every 0.28 microseconds to obtain anatomical information. Thus, the reflected ultrasound is sampled about 174 times following each burst for providing the blood flow image and more frequently for providing the anatomical image. The returning ultrasound received during the early time intervals are reflected from body structure and blood cells in proximity to probe 10. Ultrasound received during later intervals is reflected from sources deeper in the body. The amplitude and timing of the reflected ultrasound are used to generate conventional, two-dimensional anatomical imaging information of body structure, such as the heart structure image 16 depicted in FIG. 1. Apparatus is also provided for displaying body structure in white.

Movement of a reflecting body, such as a group of blood cells, away from probe 10 increases the wavelength of the reflected ultrasound, whereas movement of the body toward the probe decreases the wavelength according to the Doppler principle. Given the speed of sound in tissue and the frequency of the ultrasound, human blood velocities will produce such Doppler shifts on the order of 200 Hz to 8 KHz. As will be seen, a total of 5 separate ultrasound bursts are generated to provide velocity information at points along 64 separate beam directions throughout angle $\phi$ in order to form scan image 14. The image color and intensity (not shown) is adjusted in accordance with the direction and velocity of flow. Velocity information for blood flow away from the probe is shown in red whereas information on blood flow toward the probe is shown in blue. The greater the magnitude of the velocity, the brighter the image. Thus, for example, the blood flow image in region 18 adjacent the aorta valve would be bright red, since blood flow in this region is away from probe 10 at a relatively high velocity.

Although the subject ultrasound apparatus is capable of superimposing blood flow information over the entire sector scan image 14, it is usually preferable to display such information only over a fraction of the scan angle $\phi$. The anatomical data portion of the image is typically formed from 128 beams, or rays, of picture elements or pixels, for a full scan. A full scan of blood flow data would be comprised of 64 beams, or rays, of pixels. However, because of the relatively low rate at which the blood flow pixel data are produced, the image produced from a full scan of blood flow data tends to flicker. Although such flicker may be acceptable in some applications, it is usually preferable to limit the scan angle of blood flow information to some fraction of the anatomical scan angle $\phi$. For example, a blood flow scan angle of approximately one-half that of the anatomical angle, comprising 30 beams of pixel data, substantially reduces flicker. In order to obtain the benefits of the subject invention, blood flow image data over at least two beam directions should be used, although multiple beam directions are prefered so as to provide a more complete image. The fraction of the scan angle over which blood flow information produced can be controlled by the operator. In addition, the depth of the blood flow information can be reduced to a fraction of that of the anatomical data. For example, if anatomical information down to a depth of 15 cm. in the body is displayed, the operator can limit the processing of blood flow information to 10 cm. in order to improve the characteristics of the blood flow image. Again, suitable controls are provided (not shown) to enable the operator to adjust the maximum depth at which blood flow data is processed.

Figure 2B:
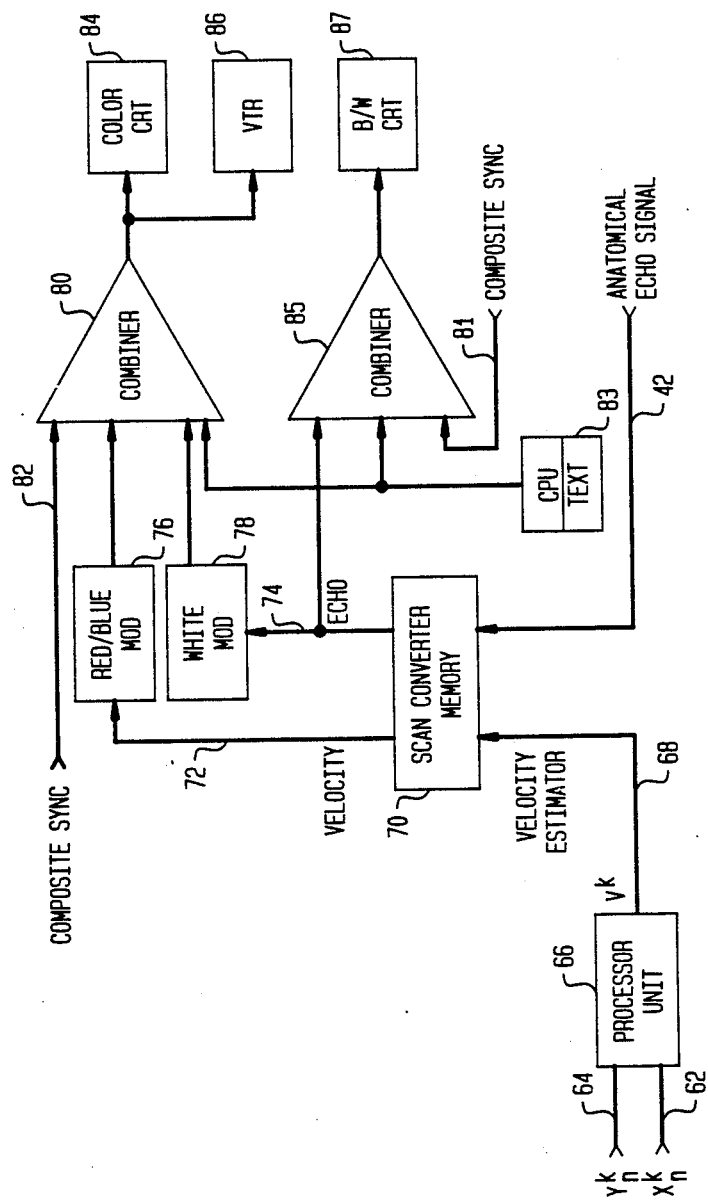

Referring now to FIGS. 2A and 2B, the subject ultrasound apparatus includes a reference oscillator 20 which provides a 3.0 MHz output signal on line 22. The reference frequency is selected to be the operating frequency of the transducer probe. A pulse generator 24, which is coupled to the reference oscillator 20, produces a series of bursts or pulses of the 3.0 MHz signal. The individual bursts are each typically 0.33 microseconds duration, with a series of bursts lasting no more than 8 microseconds. The series of pulses, referred hereinafter as bursts, are produced every 200 microseconds.

The output of pulse generator 24 is connected to a plurality of phased array pulser circuits represented by block 26. There are typically 48 separate pulser circuits. Each pulser circuit has a digitally selected delay. The output of each pulser circuit is connected to an individual piezoelectric transducer 28 of a transducer array located within probe 10. The piezoelectric transducers convert the 3 MHz bursts or pulses provided by the pulser circuits 26 to ultrasound. The delays of the individual pulser circuits are controlled by conventional control circuitry (not shown) to produce a series of beams of ultrasound which are steered over angle $\phi$ so as to provide the standard sector scan image 14 (FIG. 1).

Figure 7:
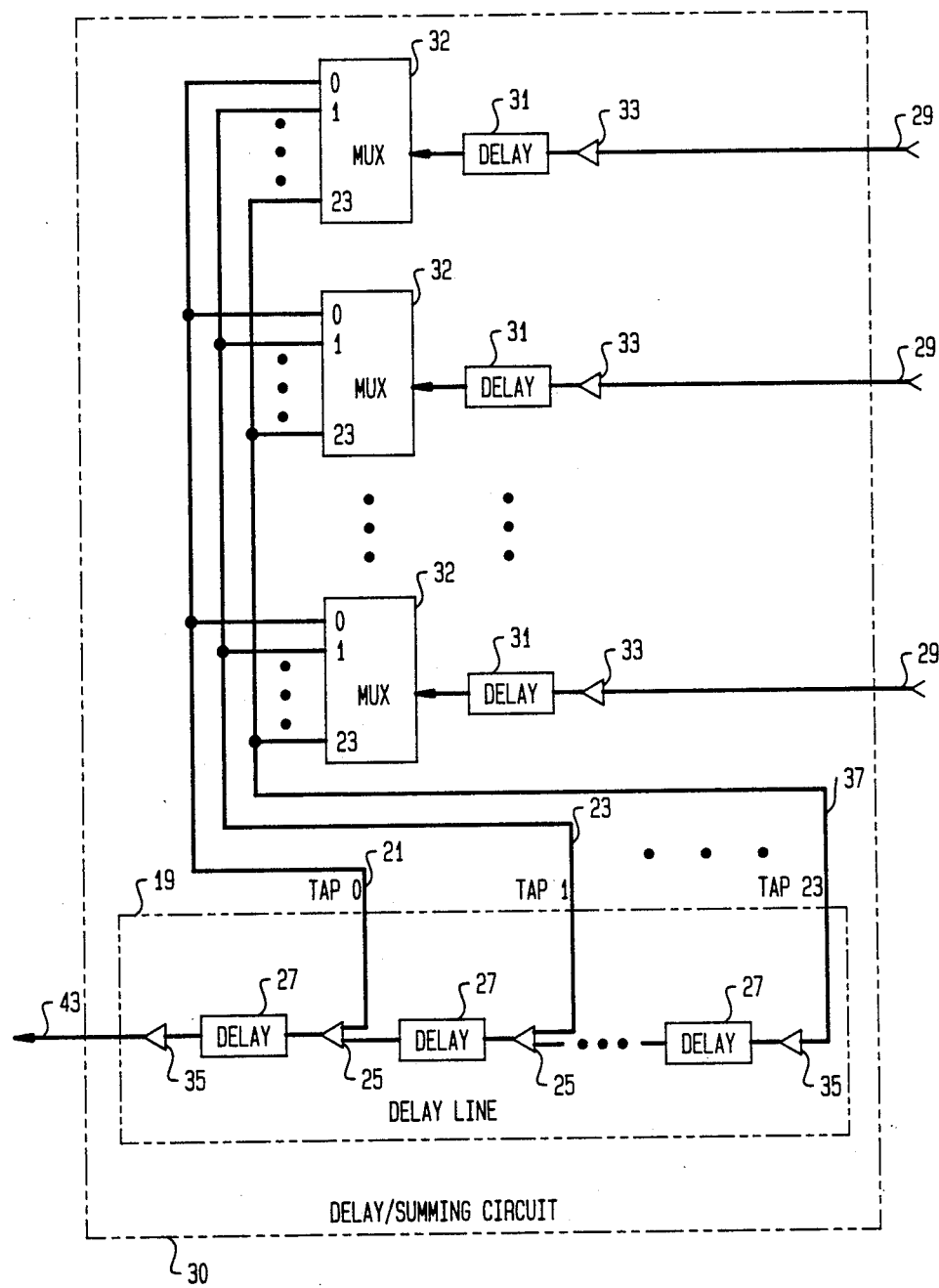
FIG. 7 shows further details of the summing/delay circuit of the subject ultrasound diagnostic apparatus.

Piezoelectric transducers 28 are also connected to a plurality of receiver circuits represented by block 10. During the 190 microsecond intervals between ultrasound transmissions, transducers 28 serve as ultrasound receivers and convert the reflected ultrasound to electrical signals. The electrical signals are fed to a delay/summing circuit 30 which provides a controllable delay for each transducer 28 output of probe 10 and sums the outputs together. As is well-known, it is necessary to selectively delay the signals provided by each transducer of a phased transducer array so that signals produced by ultrasound reflections from a single source in the body are processed simultaneously. FIG. 7 shows further details of the delay/summing circuit 30. The 48 outputs of transducers 28 on lines 29 are each coupled to a preamplifier circuit 33. The outputs of amplifiers 33 are each connected to a variable short-delay circuit 31 having a digital control input (not shown) which permits the delay of each circuit 31 to be selectively varied by control apparatus (not shown) from a 0 to 0.32 microseconds.

The outputs of the forty eight short-delay circuits 31 are each connected to the input of one of 48 analog multiplexers 32, each having 24 outputs. Each multiplexer has a control input (not shown) which causes the analog signal at the input to be coupled to a selected one of the 24 outputs of the multiplexer 32. Each of the 24 outputs of the 32 is connected to a tap on a delay line 19. Outputs 0, for example, of each of the multiplexers 32 are fed to TAP 0 of delay line 19, as represented by line 21. Outputs 1 are fed to TAP 1 of the delay line 19, as represented by line 23. Outputs 2 through 22 (not shown) of multiplexers 32 are connected to TAPs 2 through 22 of delay line 19. Finally, outputs 23 of the multiplexers 32 are connected to TAP 23 of the analog delay line 19, as represented by line 37.

Delay line 19 includes 24 separate analog fixed-delay circuits 27, each of which provides 300 nanoseconds of delay. TAP 0 of the circuit is connected to one input of a first two-input summing amplifier 25. The output of the amplifier 25 is connected to the input of one of the delay circuits 27. The output of delay circuit 27 is connected to the output line 43 via a buffer amplifier 35. Thus, signals on outputs 0 of multiplexers 32 will be delayed by 300 nanoseconds by delay line 19.

TAP 1 of delay line 19 is connected to one input of a second two-input summing amplifier 25. The output of amplifier 25 is connected to the second input of the first summing amplifier 25 through a second delay circuit 27. Thus, signals from multiplexer outputs 1, which are fed to TAP 1, will be delayed a total of 600 nanoseconds. The remainder of the delay circuits 27 and summing amplifiers 25 are associated with TAPS 3 through 22 and are configured in the same manner. Finally, TAP 23 of the delay line 19 is connected to the input of another delay circuit 27 through another buffer amplifier 35. Signals from outputs 23 of the multiplexers 32 which are fed to TAP 23, will be delayed a total of 7,200 nanoseconds (300 nanoseconds × 24).

The above-described implementation of delay/summing circuit 30 permits relatively large amounts of delay, on the order of 7 microseconds, to be provided at low cost. By controlling short-delay circuits 31 and multiplexers 32, using suitable control circuitry (not shown), delays are provided which cause the signals out of transducers 28 produced by ultrasound reflected from a given source to be summed and presented simultaneously on output line 43.

According to FIG. 2A the output of delay/summing circuit 30 is connected to an absolute value detector circuit 36 which produces a positive output signal proportional to the amplitude of the A.C. signal produced by delay/summing circuit 30. Circuit 36 is followed by a low pass filter circuit 38 which removes the remaining A.C. component of the signal produces by circuit 36. Thus, absolute value circuit 36, together with filter circuit 38, serves as an amplitude detector. The D.C. output of filter circuit 38 is fed to a flash analog-to-digital converter 40 which provides a digital anatomic echo signal as output 42. As is well known, flash-type converters are capable of rapidly processing data and typically do not require an associated sample-and-hold circuit. As will be subsequently described, this digital signal is transmitted to a scan converter memory for converting the sector scan output to a raster scan format for display on a black and white and a color CRT or for recording on a video tape recorder.

The output of delay/summing circuit 30 is also fed to inputs of a pair of phase detectors 42 and 44. The remaining input of detector 42 is connected to line 22 which carries the 3 MHz output signal from reference oscillator 20. The remaining input of detector 44 is connected to a phase shift circuit 46 which is in turn coupled to oscillator 20. Circuit 46 provides a 3 MHz signal to phase detector 44 which is shifted 90 degrees with respect to the reference signal provided to phase detector 42.

The outputs of phase detectors 42 and 44 are filtered by low pass filters 48 and 50, respectively. The filtered outputs are each connected to separate sample-and-hold circuits 52 and 54 which are activated by a common control circuit 56. The outputs of sample-and-hold circuits 52 and 54 are connected to the inputs of ten bit analog-to-digital converter circuits 58 and 60, respectively. The converters 58 and 60 are also connected to control circuit 56. The outputs of converters 58 and 60 are connected to output lines 62 and 64, respectively.

Phase detector 42 and filter 48 serve as an in-phase synchronous detector and phase detector 44 and filter 50 serve as a quadrature-phase synchronous detector. Control circuit 56 causes the outputs of the two detectors to be periodically sampled and held for conversions to ten bit digital signals by converters 58 and 60. The digital outputs of converters 58 and 60 represent the magnitude and sign of the in-phase and quadrature phase components, respectively, of the reflected ultrasound signal at the reference frequency which is the operating frequency of probe 10.

Referring now to FIG. 2B, outputs of analog-to-digital converters 58 and 60 on lines 62 and 64 are fed to a processor unit 66. As will be described later in greater detail, processor unit 66 produces velocity estimator signals on output line 68 which represent the velocity of blood flow at a particular point along one of 64 beam directions spaced through angle φ (FIG. 1). The velocity estimator signals are sequentially written into a random-access scan converter memory 70 as the estimators are produced. The digital anatomic echo signals on line 42 are also sequentially written into another portion of scan converter memory 70 as these signals are generated.

The velocity estimator signals and anatomical echo signals are read out of the scan converter memory 70 on lines 72 and 74, respectively, in a standard raster scan format. The velocity estimator and anatomical echo signals associated with a particular segment of the body are read out of separate areas of the memory 70 at essentially the same time. The velocity estimator signals control a red/blue color modulator circuit 76. The output of color modulator circuit 76 is connected to an input of a combiner circuit 80. The anatomical echo signal data read out of the converter memory 70 are coupled to a white modulator circuit 78, having an output which is connected to another input of combiner circuit 80. Combiner circuit 80 has a third input connected to a line 82 which carries a conventional composite video synchronization signal. This signal includes, for example, the horizontal and vertical syncs. A color burst signal (not shown) is also fed to the combiner 80. A fourth combiner input is connected to the output of a Central Processor Unit (CPU) 83. CPU 83, among other things, provides textual information including, for example, the name of the patient, medical history and operating instructions which may be selected from a menu in the conventional manner. The output of combiner circuit 80 drives both a color cathode ray tube 84 (CRT) and a video tape recorder 86 (VTR). The anatomical and blood flow data are superimposed by simply summing the two signals in the combiner 80. The subject ultrasound apparatus also preferably includes a black and white television monitor for displaying anatomical information exclusively. The monitor display includes a black and white CRT 87 which is driven by a second combiner circuit 85. One input of combiner 85 is connected to line 74 which carries the anatomical echo data read from scan converter memory 70. A second input is connected to a line 81 which carries a composite video synchronization signal. A third input is connected to central processor unit (CPU) 83.

Operation of the subject ultrasound diagnostic apparatus will now be given in greater detail. As previously described, a pulsed beam of ultrasound energy is periodically transmitted from the phased transducer array of probe 10. The beams sweep over angle φ to produce sector scan image 14 (FIG. 1). For each of 64 beam directions, pulse generator 24 (FIG. 2A) causes the probe to transmit five bursts of ultrasound approximately 200 microseconds apart. A signal is produced at the output of delay/summing circuit 30 from the reflected ultrasound following each burst. If the reflecting source is moving with respect to the transmitted ultrasound, the reflected signal will have a frequency shift which is proportional to the component of the velocity of the source towards the probe 10. Filter 48 will provide a signal having a sign and magnitude which corresponds to the in-phase component of the reflected signal with respect to the reference frequency and filter 50 will provide a signal having a sign and magnitude which corresponds to the quadrature-phase component of the reflected signal with respect to the reference frequency. These analog signals are sampled and converted to digital signals once every 1.12 microseconds by sample-and-hold circuits 52, 54 and converter circuits 58, 60.

The digital data produced by the analog-to-digital converters 58, 60 associated with the in-phase demodulator and the quadrature-phase demodulator are denoted as $X_n^k$ and $Y_n^k$, respectively. The subscript n varies from 0 to 4 and indicates which of the five ultrasound bursts (beamline type) along a beam direction produced the data. The superscript k varies from 0 to 173, and indicates which of the 174 successive samples of reflected ultrasound produced the data. Thus, for example, $X_2^{60}$ represents the in-phase component produced during the sixty-first time interval following the transmission of a beamline type 2 (the third of five bursts).

The digital velocity estimator signals at the output of processor unit 66 represent the sign and magnitude of the blood velocity at a given point along one of the 64 beam directions. As previously noted, the user will typically adjust the subject diagnostic apparatus to limit the number of beam directions to less than 64 to improve the quality of the blood flow image. The signals may be either negative or positive, depending on the direction of blood flow with respect to probe 10. The estimators are denoted by $V^k$ where superscript k again indicates the position of the blood sample along the beam line. Thus, for example, velocity estimator $V^{100}$ would represent the velocity of a volume of blood which would be displayed on image 14 of FIG. 1 somewhat more than halfway down the image. If the five ultrasound bursts were transmitted in the direction along beam line 88, for example, the resultant velocity estimator $V^{100}$ would represent the velocity of blood flow in region 18 adjacent the aorta valve. An estimator $V^{130}$ produced by the same five bursts would represent the velocity of blood flow deeper in the heart in region 90.

The velocity estimators $V^k$ are computed by processor unit 66 from values $X_n^k$ and $Y_n^k$ in accordance with the following equation:

$$V^k = + |(X_0^k S_0 - Y_0^k T_0 + X_1^k S_1 - Y_1^k T_1 + X_2^k S_2 - \quad (1)$$
$$Y_2^k T_2 + X_3^k S_3 - Y_3^k T_3 + X_4^k S_4 - Y_4^k T_4)| +$$
$$|(X_0^k T_0 + Y_0^k S_0 + X_1^k T_1 + Y_1^k S_1 + X_2^k T_2 +$$
$$Y_2^k S_2 + X_3^k T_3 + Y_3^k S_3 + X_4^k T_4 + Y_4^k S_4)| -$$
$$|(X_0^k S_0 + Y_0^k T_0 + X_1^k S_1 + Y_1^k T_1 + X_2^k S_2 +$$
$$Y_2^k T_2 + X_3^k S_3 + Y_3^k T_3 + X_4^k S_4 + Y_4^k T_4)| -$$
$$|(X_0^k T_0 - Y_0^k S_0 + X_1^k T_1 - Y_1^k S_1 + X_2^k T_2 -$$
$$Y_2^k S_2 + X_3^k T_3 - Y_3^k S_3 + X_4^k T_4 - Y_4^k S_4)|$$

where $V$ = velocity estimator;
$k$ = time interval (0-173);
$X$ = in-phase component of demodulator output data;
$Y$ = quadrature-phase component of demodulator output data;
$S_0 = 1$; $S_1 = -4$; $S_2 = 6$; $S_3 = -4$; $S_4 = 1$; $T_0 = -2$; $T_1 = 4$; $T_2 = 0$; $T_3 = -4$; and $T_4 = 2$.

Figure 3:
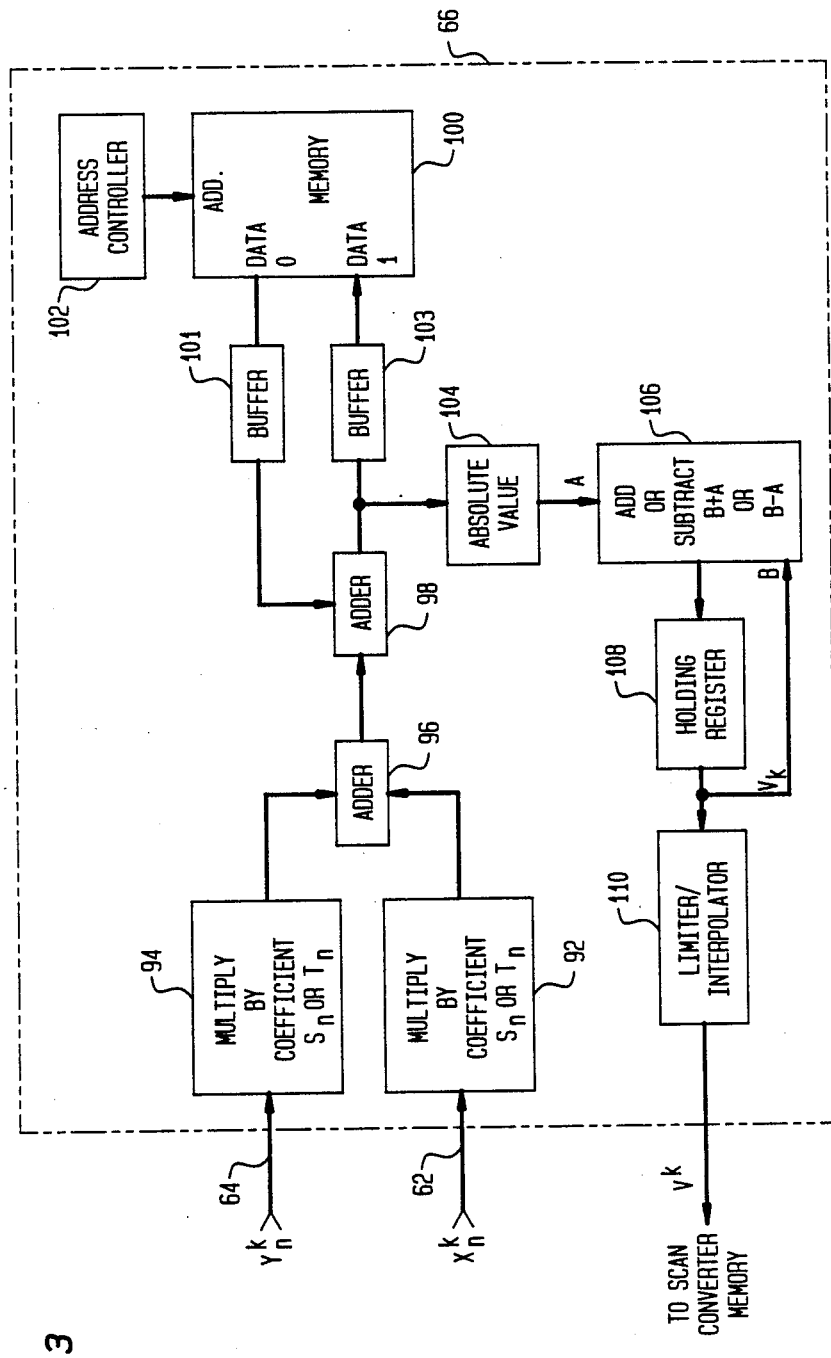
FIG. 3 is a block diagram showing further details of the processor unit of the subject ultrasound diagnostic apparatus.

Reference is now made to FIG. 3 for a further explanation of the operation of processor unit 66 and the manner in which the computation represented by equation (1) is carried out. Processor unit 66 is implemented utilizing conventional hardwired logic elements rather than a programmed microprocessor because of computational speed requirements. The particular implementation of the processor could easily be accomplished in various ways by a person of average skill based upon the present disclosure. Rather than obscuring the true nature of the subject invention in unnecessary detail, operation of processor unit 66 will be described in a functional manner.

The demodulated in-phase components $X_n^k$ are multiplied by constant coefficients $S_n$ or $T_n$ as represented by block 92 of FIG. 3. Similarly, the quadrature-phase components $Y_n^k$ are also multiplied by these coefficients as represented by block 94. The resultant respective products are then added together as represented by a first adder 96 and forwarded to a second adder 98. Adders 96 and 98 are both capable of performing subtract operations. The remaining input of adder 98 is connected to the output of a buffer 101. The output of adder 98 is coupled to the data input of a read-only-memory 100. The data output of memory 100 is connected to the input of buffer 101. An address controller 102 is provided for generating memory addresses as required.

The output of adder 98 is also connected to an absolute value circuit 104 which in turn, has an output connected to the input of Add Or Subtract circuit 106. The output of circuit 106 is connected to the input of a holding register 108, with the output of register 108 being connected back to the second input of circuit 106. The output of register 108 is also connected to the input of a limiter/interpolater circuit 110, the output of which serves as the output of the processor.

Figure 4:
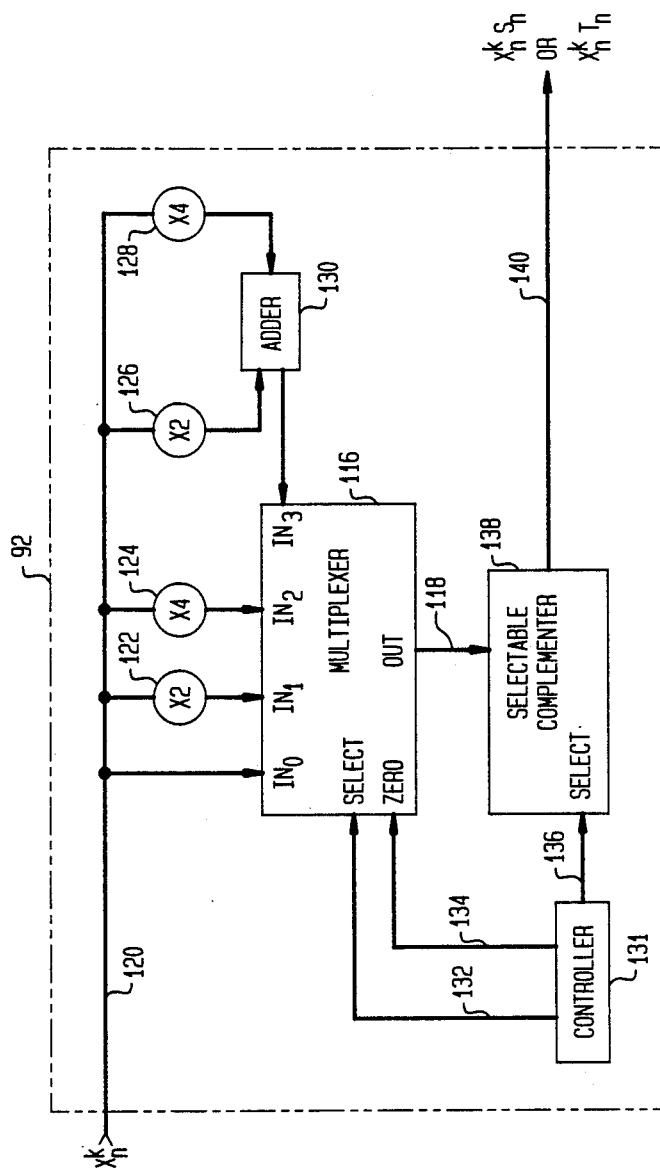
FIG. 4 is a block diagram of the coefficient multiplier sections of the processor unit.

Referring now to FIG. 4, additional details of the coefficient multiplication circuit 92 of the processor will be given. Circuit 94, which is associated with the quadrature-phase data, $Y_n^k$, operates in a similar manner.

Multiplication circuit 92 includes a four-input multiplexer circuit 116. Multiplexer 16 is capable of transferring thirteen bits of parallel data present on the selected one of the four inputs to the output on line 118. The 10 bits of $X_n^k$ data on line 120 are fed directly to input $IN_0$ of multiplexer 116. The $X_n^k$ data fed to input $IN_1$ is multiplied by 2 by multiplier circuit 122. Circuit 122 simply consists of wiring the least significant bit of $IN_1$ to the next-to-least significant bit of $X_n^k$, and so forth, so that all bits are shifted by one place in wiring $X_n^k$ to $IN_1$. The $X_n^k$ data coupled to input $IN_2$ is multiplied by 4 by multiplier circuit 124. Circuit 124 accomplishes the multiplication function simply by having the ten bits of $X_n^k$ data on line 120 shifted by two positions as they are wired to $IN_2$. Finally, the $X_n^k$ data applied to input $IN_3$ is multiplied by 6. The multiplication is accomplished by multiplying the $X_n^k$ data on line 120 by 2 through circuit 126 and by 4 through circuit 128 and adding the results together using adder 130. Circuits 126 and 128 are similar to multiplier circuits 122 and 124, respectively.

Multiplication circuit 92 further includes control logic 131 which produces digital signals on output lines 132, 134 and 136 in a predetermined sequence. The output on line 132 is two bits of data which are fed to the Select input of multiplexer 116. The two bits of data on line 132 control which of the four inputs of the multiplexer is fed to the output. If constants S or T are to be either ±1, input $IN_0$ is selected. If the constants are to be either ±2, input $IN_1$ is selected and if the constants are to be either ±4, input $IN_2$ is selected. Finally, if constants S or T are to be either ±6, input $IN_3$ is selected.

The output line 134 of controller 131 is connected to the Zero input of multiplexer 116. If a signal is applied to this input, the output of the multiplexer 116 is all zeros. Thus, if constants S or T are to be zero, controller 131 will produce a signal on line 134.

The 16 bit parallel output of multiplexer 116 is fed, as indicated by line 118, to a selectable complementer circuit 138 which is controlled by the output of controller 131 via line 126. If no signal is present on line 136, complementer circuit 138 generates a digital output on line 140 which is identical to the data applied to the input of the circuit 138. A signal on line 136 will cause the outputed data on line 140 to be the complement of the data out of multiplexer 116. Thus, if either constant S or T is to be negative, controller 131 will produce a signal on line 136.

The function accomplished by complementer 138 is actually implemented indirectly. If both the $X_n^k$ and $Y_n^k$ data need to be conplemented, the positive data are first added by adder 96 (FIG. 3) and forwarded to adder 98. Adder 98 is then directed to perform a subtract operation. If the $Y_n^k$ data only need to be complemented, adder 96 is directed to perform a subtract operation. Finally, if just the $X_n^k$ data are to be complemented, both adders 96 and 98 are directed to perform subtract operations.

During a beamline type 0 (n=0), which occurs during the 190 microsecond sampling period following the first of the five ultrasound bursts along a beam direction, adder 96 (FIG. 3) generates a sequence of values as shown in Table 1.

TABLE 1

$X_o^oS_o - Y_o^oT_o$
$X_o^oT_o + Y_o^oS_o$
$X_o^oS_o + Y_o^oT_o$
$X_o^oT_o - Y_o^oS_o$
$X_o^1S_o - Y_o^1T_o$
$X_o^1T_o + Y_o^1S_o$
$X_o^1S_o + Y_o^1T_o$
$X_o^1T_o - Y_o^1S_o$
$X_o^2S_o - Y_o^2T_o$
$X_o^2T_o + Y_o^2S_o$
ETC.

The first four values of Table 1 are computed from demodulator output signals $X_o^o$, these being the first samples (k=o) of the demodulator data for the beamline. During the next time interval (k=1), which is the next 1.12 microsecond time interval, demodulator outputs are sampled again, yielding the data pair $X_o^1$ and $Y_o^1$. The next four output values of Table 1 are derived from this new data. This process continues for each of the remaining intervals following the transmission of the first (n=0) ultrasound burst (k=2 through 173.

Each time adder 96 completes an operation, the sum is fed to the second adder 98. At the same time, data is read out of random-access-memory 100 and is transferred to the buffer register 101. The output of register 101 is coupled to the second input of adder 98 for addition to the data provided by adder 96. The sum is then loaded into a second buffer register 103 and then back into memory 100 at the same address from which data was previously read out. Memory addressing is accomplished using an address controller 102. Memory 100 is preferably fabricated from high speed static random-access memories. Four 2K word by 8 bit CMOS memories, manufactured by Hitachi under the designation HM6116-P2 have been found suitable for this purpose.

During a beamline type 0 (n=0), data read from memory 100 and then fed to adder 98 is forced to all zeros by activating the reset control on buffer 101. This does not occur in other beamline types (n=1-4). The zero data of beamline type 0 is then summed by adder 98 with the data from adder 96 to produce the values shown in Table 1. The sums are then stored in memory 100.

A separate area of memory 100 is reserved for each pair of demodulator samples ($X^k$ and $Y^k$). Each area has four addresses. During the beamline type 0, the four addresses for the first demodulator pair ($X_o^o$ and $Y_o^o$) will hold the four values shown in Table 2.

TABLE 2

| $X_o^oS_o - Y_o^oT_o$ |
|---|
| $X_o^oT_o + Y_o^oS_o$ |
| $X_o^oS_o + Y_o^oT_o$ |
| $X_o^oT_o - Y_o^oS_o$ |

During the remainder of beamline type 0, the four values associated with each of the subsequent 173 data samples (k=1-173) will be stored in additional memory locations.

During the next beamline type (n=1), the values produced by adder 98 are shown in Table 3.

TABLE 3

| $X_1^oS_1 - Y_1^oT_1$ |
|---|
| $X_1^oT_1 + Y_1^oS_1$ |
| $X_1^oS_1 + Y_1^oT_1$ |
| $X_1^oT_1 - Y_1^oS_1$ |
| $X_1^1S_1 - Y_1^1T_1$ |
| $X_1^1T_1 + Y_1^1S_1$ |
| $X_1^1S_1 + Y_1^1T_1$ |
| $X_1^1T_1 - Y_1^1S_1$ |
| $X_1^2S_1 - Y_1^2T_1$ |
| $X_1^2T_1 + Y_1^2S_1$ |
| ETC. |

The values of Table 3 are sequentially forwarded to adder 98 to be summed with the corresponding values which were loaded into memory 100 during the previous beamline type (n=o). The initial beamline type 0 values are shown in Table 1. The added result, which is shown in Table 4, is stored back in memory 100 at the same locations.

TABLE 4

| $X_o^oS_o - Y_o^oT_o + X_1^oS_1 - Y_1^oT_1$ |
|---|
| $X_o^oT_o + Y_o^oS_o + X_1^oT_1 + Y_1^oS_1$ |
| $X_o^oS_o + Y_o^oT_o + X_1^oS_1 + Y_1^oT_1$ |
| $X_o^oT_o - Y_o^oS_o + X_1^oT_1 - Y_1^oS_1$ |
| $X_o^1S_o - Y_o^1T_o + X_1^1S_1 - Y_1^1T_1$ |
| $X_o^1T_o + Y_o^1S_o + X_1^1T_1 + Y_1^1S_1$ |
| $X_o^1S_o + Y_o^1T_o + X_1^1S_1 + Y_1^1T_1$ |
| $X_o^1T_o - Y_o^1S_o + X_1^1T_1 - Y_1^1S_1$ |
| $X_o^2S_o - Y_o^2T_o + X_1^2S_1 - Y_1^2T_1$ |

TABLE 4-continued

| $X_o^2T_o + Y_o^2S_o + Y_1^2T_1 + Y_1^2S_1$ |
|---|
| ETC. |

The same sequence is repeated for the following three beamline types (n=2-4). During the last, or fifth beamline type (n=4), memory 100 is updated with the values shown in Table 5.

TABLE 5

| $X_o^oS_o - Y_o^oT_o + X_1^oS_1 - Y_1^oT_1 + X_2^oS_2 - Y_2^oT_2 + X_3^oS_3 - Y_3^oT_3 + X_4^oS_4 - Y_4^oT_4$ |
|---|
| $X_o^oT_o + Y_o^oS_o + X_1^oT_1 + Y_1^oS_1 + X_2^oT_2 + Y_2^oS_2 + X_3^oT_3 + Y_3^oS_3 + X_4^oT_4 + Y_4^oS_4$ |
| $X_o^oS_o + Y_o^oT_o + X_1^oS_1 + Y_1^oT_1 + X_2^oS_2 + Y_2^oT_2 + X_3^oS_3 + Y_3^oT_3 + X_4^oS_4 + Y_4^oT_4$ |
| $X_o^oT_o - Y_o^oS_o + X_1^oT_1 - Y_1^oS_1 + X_2^oT_2 - Y_2^oS_2 + X_3^oT_3 - Y_3^oS_3 + X_4^oT_4 - Y_4^oS_4$ |
| $X_o^1S_o - Y_o^1T_o + X_1^1S_1 - Y_1^1T_1 + X_2^1S_2 - Y_2^1T_2 + X_3^1S_3 - Y_3^1T_3 + X_4^1S_4 - Y_4^1T_4$ |
| $X_o^1T_o + Y_o^1S_o + X_1^1T_1 + Y_1^1S_1 + X_2^1T_2 + Y_2^1S_2 + X_3^1T_3 + Y_3^1S_3 + X_4^1T_4 + Y_4^1S_4$ |
| $X_o^1S_o + Y_o^1T_o + X_1^1S_1 + Y_1^1T_1 + X_2^1S_2 + Y_2^1T_2 + X_3^1S_3 + Y_3^1T_3 + X_4^1S_4 + Y_4^1T_4$ |
| $X_o^1T_o - Y_o^1S_o + X_1^1T_1 - Y_1^1S_1 + X_2^1T_2 - Y_2^1S_2 + X_3^1T_3 - Y_3^1S_3 + X_4^1T_4 - Y_4^1S_4$ |
| $X_o^2S_o - Y_o^2T_o + X_1^2S_1 - Y_1^2T_1 + X_2^2S_2 - Y_2^2T_2 + X_3^2S_3 - Y_3^2T_3 + X_4^2S_4 - Y_4^2T_4$ |
| $X_o^2T_o + Y_o^2S_o + X_1^2T_1 + Y_1^2S_1 + X_2^2T_2 + Y_2^2S_2 + X_3^2T_3 + Y_3^2S_3 + X_4^2T_4 + Y_4^2S_4$ |
| ETC. |

The first four values stored in memory 100 during the last beamline type (n=4) as shown in Table 5, correspond to the four terms used to compute the velocity estimator $V^o$ as can be seen from equation (1). Similarly, the next four terms stored in the memory 100 are used to compute the velocity estimator $V^1$. Each of the following four consecutive values stored in the memory 100 at this time is used to compute the remaining velocity estimators $V^2$ through $V^{173}$ in the same manner along a particular beam direction.

Referring now to FIG. 5A, the timing sequence for a fraction of a sector scan will be further described. Line A of the FIG. 5A timing diagram depicts the beam directions along which ultrasound is transmitted to produce blood flow data over approximately one-half of a complete sector scan. A total of 64 beam directions would be used to provide blood flow information over the entire scan. As shown, a total of 30 beam directions is used for a half scan, with each direction being assigned a direction number 0 through 29. Line B of the diagram shows the elapsed time in microseconds. A one-half scan requires approximately 30 milliseconds, with beam direction changes occuring every 1 millisecond.

Lines B, C, D and E of FIG. 5A depict the expanded time period during direction line numbers 1 and 2 of the scan. As indicated by line D, there are five beamline types (0-4) which occur in each beam direction. Each beamline is approximately 200 microseconds in duration.

The time period of beamline type 3 of beam direction number 1 is depicted in lines F and G. This period falls between 1600 and 1800 microseconds points of the scan. During approximately the first 8 microsecond period, probe 10 transmits ultrasound. During the remaining 192 microsecond period, the probe 10 acts as a receiver, and detects reflected ultrasound. An exemplary expanded segment of the receive interval is depicted in line H. This segment falls between the 1616.00 microsecond point and the 1621.60 microsecond point of the scan.

Figure 5B:
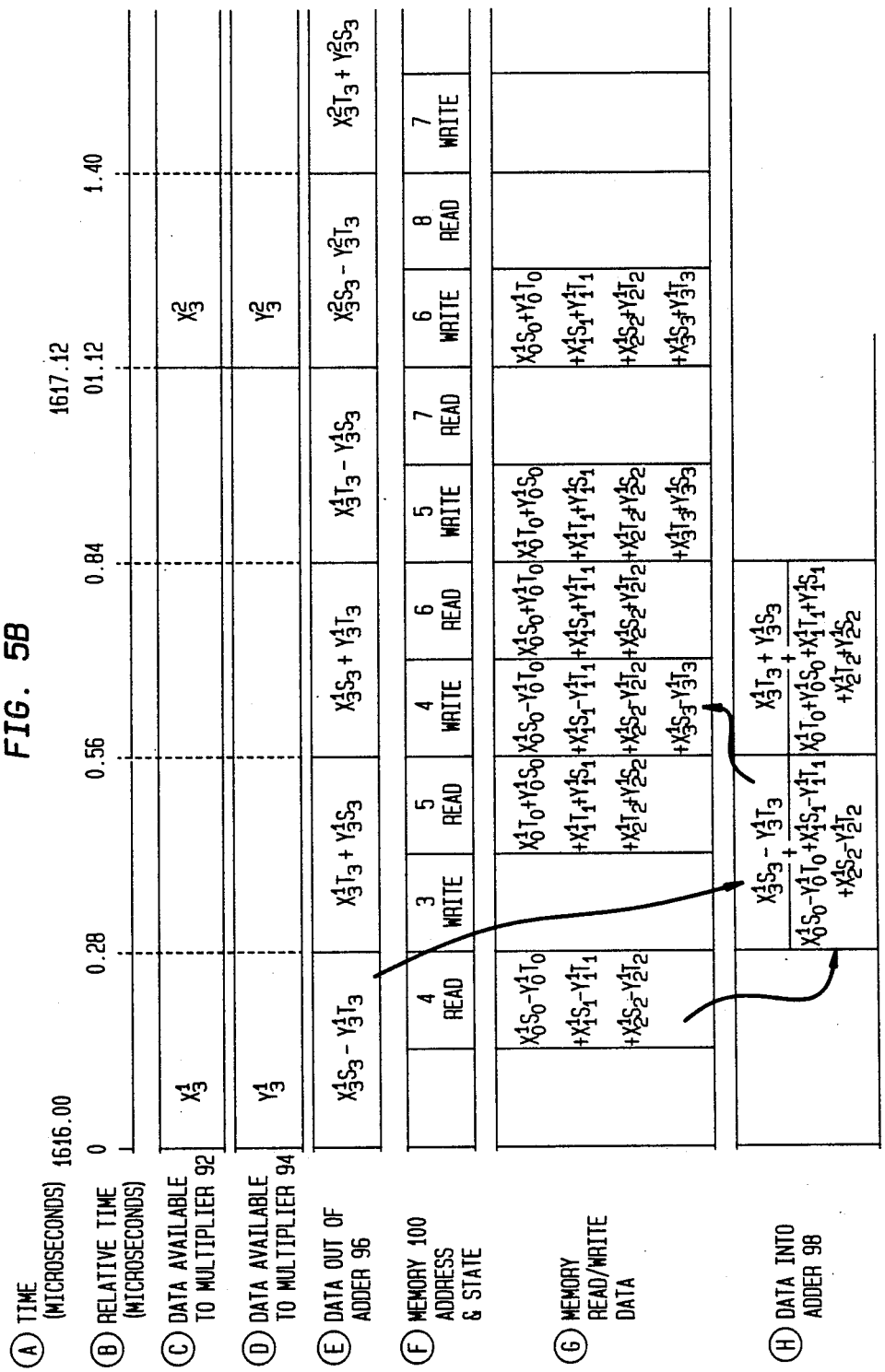

Referring now to FIG. 5B, memory 100 read and write operations of processor unit 66 and related events will now be further described. The time interval depicted in line H of FIG. 5A, which occurs during the beamline type 3 of beam direction number 1, will be used as an example. Line A of FIG. 5B shows the time interval of the scan which is to be examined. Line B shows relative time with time zero occurring at 1616.00 microseconds into the scan. The depicted period is broken up into 0.28 microsecond intervals. At the beginning of the first 0.28 microsecond interval, the in-phase coefficient multiplier 92 (FIG. 3) is presented with signal $X_3^0$ as indicated by line C of FIG. 5B. Similarly, the quadrature-phase multiplier 94 is presented with signal $Y_3^0$ as indicated by line D. These values are updated to $X_3^1$ and $Y_3^1$, respectively, 1.12 microseconds later, as previously described.

During the initial portion of the first 0.28 microsecond interval, coefficient multiplier 92 multiplies data $X_3^0$ by $S_3$ and multiplier 94 multiplies data $Y_3^0$ by $T_3$. These values are fed to adder 96 which produces the output value $X_3^0 S_3 - Y_3^0 T_3$, as depicted on line E of FIG. 5B. Multipliers 92 and 94 perform subsequent coefficient multiplications once every 0.28 microseconds as also shown on line E.

A memory 100 write cycle, followed by a read cycle, occurs once every 0.28 microseconds. For example, as indicated by line F of FIG. 5B, the contents of memory 100 at address 4 are read out during the second half of the first 0.28 microsecond interval. The data read out of memory 100 at address 4 at this time are shown in line G and are temporarily held in buffer 101 (FIG. 3). During the first half of the next 0.28 microsecond interval, beginning at relative time 0.28 microseconds, data are written into memory address 3. These data are not used until the next beamline type and are not depicted. Also at this time, the content of buffer 101, shown on line G, which was just read out from address 4, is added to the data outputed by adder 96. This addition, which is performed by adder 98, is depicted in line H and the sum is held temporarily in buffer 103 (FIG. 3).

During the final half of the 0.28 microsecond interval, ending at relative time 0.56 microseconds, the contents of memory 100 at address 5 are read out and stored in buffer 101 as depicted in lines F and G. The output of adder 98 stored in buffer 103 is then written into memory 100 at address 4 during the first half of the next 0.28 microsecond interval beginning at relative time 0.56 microseconds, as depicted in lines F and G.

The above-described alternating read/write sequence is repeated until four memory 100 locations (addresses 4-7) have beamline type 3 data for k=1 stored in them. The sequence will then be repeated for k=2, beginning at relative time 1.12 microseconds at which time memory addresses 8-11 will commence to be loaded with beamline type 3 data. The memory loading sequence will be repeated for the remainder of the type 3 data. During the next and final beamline (type 4), the data in memory 100 will be combined with the type 4 data in the same manner as previously described. The combined data then will be sequentially fed to absolute value circuit 104 (FIG. 3), add/substract circuit 106, register 108 and limiter/interpolator circuit 110 in the manner previously described. These data circuits are not active until the beamline type 4 data are produced.

It can be seen that the various components which comprise processor unit 66 operate simultaneously in synchronization with one another. Thus, for example, coefficient multipliers 92 and 94 are operating on one group of data while adder 98 and memory 100 are operating on another group. Also, memory writes for k=1 are interleaved somewhat with memory reads for k=2, and similarly for larger values of k. Such parallel operation, sometimes referred to as "pipelining", enables data to be processed at a high rate.

As indicated by block 104, the absolute value A of the data stored in memory 100 during the final beamline line type (n=4) is sequentially computed. As further indicated by block 106, once the absolute value of a memory location is determined, the value A is either added or subtracted from a value B which was previously read out of the memory 100 and which was momentarily held in the holding register 108. The values A and B are either added or subtracted from one another in accordance with the sign preceding each of the four absolute value terms of equation (1). For example, the velocity estimator $V^0$ for the first time interval (k=0) along one of the 30 beam directions will be as follows:

$$V^0 = |(X_0^0 S_0 - Y_0^0 T_0 + X_1^0 S_1 - Y_1^0 T_1 + X_2^0 S_2 - \qquad (2)$$
$$Y_2^0 T_2 + X_3^0 S_3 - Y_3^0 T_3 + X_4^0 S_4 - Y_4^0 T_4)| +$$
$$|(X_0^0 T_0 + Y_0^0 S_0 + X_1^0 T_1 + Y_1^0 S_1 + X_2^0 T_2 +$$
$$Y_2^0 S_2 + X_3^0 T_3 + Y_3^0 S_3 + X_4^0 T_4 + Y_4^0 S_4)| -$$
$$|(X_0^0 S_0 + Y_0^0 T_0 + X_1^0 S_1 + Y_1^0 T_1 + X_2^0 S_2 +$$
$$Y_2^0 T_2 + X_3^0 S_3 + Y_3^0 T_3 + X_4^0 S_4 + Y_4^0 T_4)| -$$
$$|(X_0^0 T_0 - Y_0^0 S_0 + X_1^0 T_1 - Y_1^0 S_1 + X_2^0 T_2 -$$
$$Y_2^0 S_2 + X_3^0 T_3 - Y_3^0 S_3 + X_4^0 T_4 - Y_4^0 S_4)|$$

The function of absolute value circuit 104 is implemented indirectly. If the output of buffer 103 is negative, the normal add/subtract operation of circuit 106 is reversed. Otherwise, normal add/subtract operations occur.

Figure 6:
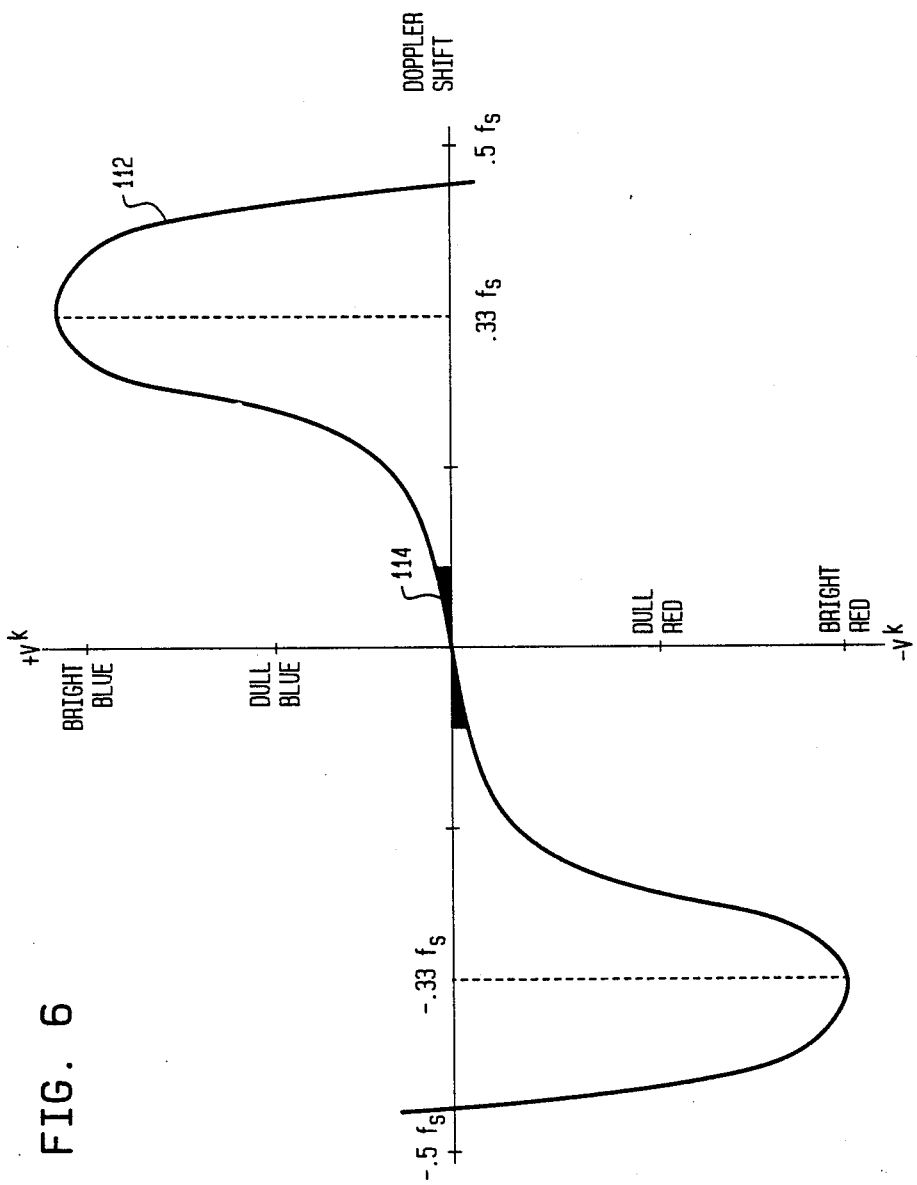
FIG. 6 shows a curve which represents the Doppler shift versus velocity estimator magnitude characteristics of the processor unit of the subject ultrasound diagnostic apparatus.

Referring now to FIG. 6, a curve 112 is depicted which generally represents the transfer characteristic or processor unit 66. The abscissa of the graph represents the Doppler shift detected in the reflected ultrasound and the ordinate represents the magnitude of the resultant velocity estimators $V^k$ produced by processor unit 66. Estimators $V^k$ magnitude and sign are expressed in terms of the color and intensity of the blood flow image produced on the display. The Doppler shift, which is proportional to the component of blood velocity in the direction of the probe is expressed in terms of the frequency $f_s$ at which ultrasound reflected from the blood volume is sampled. As previously noted, the exemplary ultrasound bursts are produced once every 200 microseconds and a particular volume of blood is sampled at the same rate. Thus, the sampling rate $f_s$ is 5 KHz.

Curve 112 is basically a plot of equation (1) where Doppler shift (blood velocity) is expressed in the equation in terms of variables $X_n^k$ and $Y_n^k$. For blood flow towards probe 10, the first two absolute value terms of equation (1) predominate and a positive value of $V_k$ is produced. For high velocity flow, the large magnitude velocity estimators will cause the color modulator 76 (FIG. 2B) to produce a bright blue output. For smaller magnitudes of blood flow velocity toward probe 10, the brightness of the blood flow image is reduced. For blood flow away from probe 10, the last two absolute value terms of equation (1) predominate and a negative value of $V^k$ is produced. For high velocity flow toward the probe, color modulator 76 will produce a bright red image. Lesser magnitude velocities in the same direction will cause the image to darken.

An important aspect of the present invention is the ability of the subject diagnostic apparatus to reject relatively low frequency Doppler signals. These signals, which are largely developed by reflections from the slow moving walls of body organs, such as the heart, interfere with the display of blood flow information. As can be seen in FIG. 6, curve 112 becomes very non-linear in the first and third quadrants of the graph in the vicinity of the origin. This inflection greatly enhances the ability of the suject device to reject low frequency Doppler signals produced by moving organ walls. Preferably, circuitry is provided which produces a black output on the display when the magnitude of $V^k$ drops below a predetermined value into a deadband 114. The inflection of curve 112 is achieved by selecting appropriate values $S_n$ and $T_n$ of equation (1), as will be subsequently described.

It is possible that high velocity blood flow will produce a Doppler shift which is comparable in magnitude to the sampling rate $f_s$. For example, as can be seen in FIG. 6, a Doppler shift which is larger than 0.33 $f_s$ will result in a reduced image brightness which is the opposite of the desired result. If the Doppler frequency is greater than 0.5 $f_s$, the color of the image will actually switch from blue to red. This phenomenon is commonly referred to as aliasing. Doppler shifts may, for example, be 3 KHZ, in which case aliasing would take place should the exemplary sampling frequency $f_s$ of 5 KHz be used. Thus, the sampling frequency should be increased. However, if the sampling frequency $f_s$ should be increased too much, it is possible that reflected ultrasound from deep within the body produced from one burst and ultra-sound reflected from a shallow segment of the body produced from the subsequent burst will be confused. This ambiguity can be avoided by limiting the processing of reflected ultrasound to a predetermined maximum depth. The maximum depth would depend on the sampling frequency and speed of sound in the body. For example, if it is necessary to increase the sampling frequency to 10 KHz in order to avoid aliasing, ambiguities can be avoided by limiting the depth from which ultrasound is processed to about 6 cm, given that the speed of ultrasound in tissue is approximately 6.5 cm/microsecond.

As previously noted, curve 112 of FIG. 6 is basically a plot of equation (1). Although this particular equation, including the values of coefficients $S_n$ and $T_n$, has been found to be preferred for the present application, other transfer functions could be used. In this regard, a further explanation of equation (1) will be given, using an intuitive approach rather than a rigorous mathematical analysis.

The Doppler signals presented to processor unit 66 can be expressed by the following equation:

$$\mathring{W}_n^k = X_n^k + jY_n^k$$

The value $\mathring{W}$ is a complex number (as indicated by °) which represents the Doppler signal. X is the in-phase component of the signal, Y is the quadrature phase component of the signal, k is the time interval, and n is the beamline type number. In the preferred embodiment, k varies from 0 to 173 and n varies from 0 through 4. Term $\mathring{W}_n^k$ can be visualized as five phasors plotted on the complex plane. The phasors are determined by the $X_n^k$ and $Y_n^k$ values generated by the detectors from the reflected ultrasound for the five beamline types. The successive phasors are produced at positions around the origin at a rate which corresponds to the detected Doppler shift of the reflected ultrasound. The direction of rotation is counterclockwise for blood flow toward probe 10, and clockwise for blood flow away from the probe 10. In the time domain, values $X_n^k$ and $Y_n^k$ would represent sinusoidal waveforms shifted 90° in phase from one another and having a frequency equal to the Doppler frequency. The $X_n^k$ waveform lags the $Y_n^k$ waveform for flow away from the probe 10 and leads $Y_n^k$ for flow towards the probe.

A second value, which is a function of $\mathring{W}_n^k$ is formed as follows:

$$\mathring{G}^k = \sum_{n=0}^{4} \mathring{W}_n^k \mathring{R}_n^*$$

The value $\mathring{R}_n^*$ is a set of 5 complex numbers with the asterisk signifying that it is the complex conjugate of the value $\mathring{R}_n$. The various values of $\mathring{R}_n$ are also selected such that the magnitude of $\mathring{G}^k$ is large when blood flow is towards probe 12. The various values of $\mathring{W}_n^k$ for blood flow in this direction may be represented by phasors which have successively larger phase angles. Thus, the phasors appear to rotate around the origin in a clockwise direction. The values of $\mathring{R}_n$ are also selected such that the magnitude of $\mathring{G}^k$ is small when the Doppler frequency is low in comparison to the sampling rate $f_s$. If the Doppler frequency is low, the successive phase shifts of the five phasors of $\mathring{W}_n^k$ will be relatively small. In the time domain, the Doppler signal waveform over the time period in which the five samples are made appears approximately as a linear ramp with a constant offset and a slight curvature. Thus, for such low Doppler frequencies, the term $\mathring{W}_n^k$ can be approximated by a constant, plus a term which varies linearly with $n-2$, (the $n-2$ term centers the waveform over the origin) plus a term which varies quadratically with $n-2$ as set forth in the following equation:

$$\mathring{W}_n^k = \mathring{a} + \mathring{b}(n-2) + \mathring{c}(n-2)^2 \quad (4)$$

The terms $S_n$ and $T_n$ of equation (1) represent the real and imaginary components of $\mathring{R}^n$ as follows:

$$\mathring{R}_n = S_n + jT_n \quad (5)$$

The five values each of $S_n$ and $T_n$ of equation (1) were selected to be insensitive to the constant, linear and quadratic functions of $(n-2)$ as set forth in equation (4). $S_n$ was chosen to be an even function of $n-2$. The following further relationships were relied upon to select the five values of $S_n$:

$$\sum_{n=0}^{4} S_n = 0 \quad (6)$$

$$4S_0 + S_1 + S_3 + 4S_4 = 0 \quad (7)$$

Equation (6) ensures insensitivity to the constant term of equation (4). Equation (7) further ensures insensitivity to the quadratic term of equation (4). In addition $S_n$ was chosen to be a symmetric function of $(n-2)$. The amplitude of $S_2$ was set arbitrarily at 6. $S_3$ and $S_4$ were chosen as $-4$ and 1, respectively, to comply with equations (6) and (7). Since $S_n$ is an even function, $S_0 = S_4 = 1$ and $S_1 = S_3 = -4$.

The values of $T_n$ were chosen as an odd function of (n−2), thereby ensuring insensitivity to the constant and quadratic terms of equation (4). Coefficient $T_3$ was arbitrarily set at −4. In order to provide insensitivity to the linear term of equation (4), the following equation was used:

$$2T_0 - T_1 + T_3 - 2T_4 = 0 \tag{8}$$

From equation (8) and the other constraints, $T_4$ was chosen as 2, $T_1 = -T_3 = 4$, and $T_0 = -2$. It should be noted that other values of $S_n$ and $T_n$ could be selected to provide insensitivity or near insensitivity to low velocity motion.

The above-noted values of $S_n$ and $T_n$ produce five complex coefficients $\mathring{R}_n$ which are distributed roughly equally around the origin of the complex plane. The coefficients are sequentially produced by processor unit 66 around the origin in the clockwise direction. As previously noted, the five values of $\mathring{W}_n^k$ can be viewed as five phasors on the complex plane which are sequentially produced at a rate equal to the sampling frequency $f_s$. If blood flow is away from probe 10, the phasors will be produced in a clockwise direction. Blood flow towards the probe 10 will cause the phasors to be generated in the counterclockwise direction.

As noted in equation (3), value $\mathring{G}^k$ is generated by adding together the five complex values produced by multiplying coefficients $\mathring{R}_n^*$ with phasors $\mathring{W}_n^k$. If the blood flow is away from probe 12, the phase angles of coefficients $\mathring{R}_n^*$ and values $\mathring{W}_n^k$ will advance in the same direction. In that case, the five products will have roughly the same phase angle and will, therefore, constructively add together when summed. If blood flow is in the opposite direction, coefficients $\mathring{R}_n$ and value $\mathring{W}_n^k$ will advance in opposite directions. The five products will have widely varying phase angles. Thus, when the products are added together, the magnitude of the final value will be small. Thus, term $\mathring{G}^k$ is relatively large for blood flow away from the probe and is relatively small for blood flow towards the probe and for low frequency Doppler produced by slow moving organ walls and blood. An additional term $\mathring{H}^k$ can be expressed as follows:

$$\mathring{H}^k = \sum_{n=0}^{4} \mathring{W}_n^k \mathring{R}_n \tag{9}$$

The terms of equation (9) are similar to those of equation (3) except that the value $\mathring{R}_n$ is used rather than the conjugate value $\mathring{R}_n^*$. Thus, if blood flows away from probe 10, the five products of equation (9) will have roughly the same phase angle and will add constructively when summed. Thus, the value $\mathring{H}^k$ will be relatively large for blood flow away from probe 10 and relatively small for flow towards the probe and relatively small for moving organ walls.

Velocity estimator $V^k$ can be determined from values $\mathring{G}^k$ and $\mathring{H}^k$ according to the following equation:

$$V^k = + |Re\,\mathring{H}^k| + |Im\,\mathring{H}^k| - |Re\,\mathring{G}^k| - |Im\,\mathring{G}^k| \tag{10}$$

The first two terms of equation (10) represent approximately the magnitude of $\mathring{H}^k$ and correspond to the first two terms of equation (1). The last two terms of equation (10) approximately represent the magnitude of $\mathring{G}^k$ and correspond to the last two terms of equation (1). As previously noted, the positive first two terms predominate when blood flow is away from probe 10 and the negative second two terms predominate when blood flow is towards the probe 10. This is illustrated by curve 112 of FIG. 6. None of the four terms are responsive to low frequency Doppler as indicated by deadband 114 of curve 112.

As also previously noted, it may be necessary to adjust the sampling frequency $f_s$ to ensure optimum operation of the subject ultrasound device. The sampling frequency should be at least twice the frequency of the maximum Doppler shift in accordance with the well-known Nyquist criterion. As can be seen from curve 112, undesirable aliasing will occur if the sampling frequency $f_s$ is less than twice the maximum Doppler shift. If the sampling frequency $f_s$ is too great, the Doppler signal will appear as a low frequency signal. As previously described, equation (10) has been optimized so as not to respond to such signals. The optimum sampling frequency $f_s$ can be determined simply by monitoring the display until an optimum blood flow image is produced.

Although it has been determined that five samples of ultrasound reflected from a particular point of the blood flow (n=0–4) have been found to produce optimum results, other values can be used. For example, it has been determined by experimentation that an adequate blood flow image can be achieved by generating velocity estimators $V^k$ from only four samples (n=0–3). The resultant response curve is, however, inferior to that of FIG. 6 in that the inflection at the origin is less pronounced. Thus, a system utilizing four samples is more susceptible to interference from slow moving organ walls. It is not believed that adequate results can be achieved by using only three samples (n=0–2) to produce velocity estimators.

It should also be noted that the number of samples can also exceed the optimum number of five. In fact, the response characteristics of curve 112 of FIG. 6 can be improved somewhat by processing a greater number of samples. However, the time required to generate a series of velocity estimators $V^k$ along a given beam direction increases as the number of samples is increased. Thus, the number of beam directions which can be displayed without substantial image flicker is reduced. The rate at which velocity estimators $V^k$ are produced can be increased by increasing the sampling frequency $f_s$. However, as previously noted, the speed of ultrasound in tissue places a limit on the maximum sampling rate. Accordingly, if the sampling rate is to be increased a large amount, a limitation must be placed on the depth to which blood velocity data is processed. Otherwise, ambiguitites will occur between ultrasound reflections from deep within the body produced by one ultrasound burst and ultrasound reflections from a shallow portion of the body which are produced by a subsequent burst.

Given the above-noted constraints, it is not believed that the benefits of the subject invention can be obtained by increasing the number of samples used to generate a velocity estimator $V^k$ to a value greater than 8 (n=0–7). The optimum value, as previously noted, is 5 samples. The preferred range of samples is 4 through 6, with samples less than 4 or greater than 8 failing to provide the full benefits of the present invention.

Referring again to FIG. 3, the velocity estimators $V^k$ are forwarded from holding register 108 to limiter/interpolator circuit 110. The limiter/interpolator circuit 110 limits the brightness of the image produced from large magnitude velocity estimators $V^k$, thereby preventing damage to the display. The limiter function is implemented using a pair of Programmable Read Only Memories (PROM) (not shown) which convert the 16-bit velocity estimator data $V^k$ to a five bit value for storage in the scan converter memory 70 (FIG. 2B). The least significant 4 bits are dropped because they are affected by digitization error. The next 5 least significant bits are used as output data unless the output data overflow. If there is positive overflow, the maximum allowable value, 01111, will be outputted from the memories. If there is negative overflow, the maximum allowable negative value of 10000 will be used. Table 6 shows the various outputs produced by the limiter function of circuit 110.

TABLE 6

| VELOCITY ESTIMATOR $V^k$ | DISPLAYED COLOR | VELOCITY |
|---|---|---|
| 01111 | BRIGHT BLUE | HIGH TOWARD PROBE |
| 01110 | . | . |
| 01101 | . | . |
| . | . | . |
| 00001 | DULL BLUE | LOW TOWARD PROBE |
| 00000 | BLACK | NO VELOCITY |
| 11111 | DULL RED | LOW AWAY FROM PROBE |
| 11110 | . | . |
| 11101 | . | . |
| . | . | . |
| 10001 | . | . |
| 10000 | BRIGHT RED | HIGH AWAY FROM PROBE |

The interpolator function of circuit 110 eliminates the borders around picture elements (pixels). The appearance of large square pixels on the display is avoided by filling the regions between successive samples (1.12 microseconds apart) with intermediate velocity values obtained by linear interpolation. This interpolation is obtained in a standard manner using a digital adder and wiring the output shifted one bit to achieve the sum divided by two, which is the average.

The conditioned velocity estimators $V^k$, as previously noted, are loaded into scan converter memory 70 (FIG. 2B) as the estimators are produced throughout the sector scan. The corresponding anatomical echo signal data are also loaded into the converter memory. Once all the data corresponding to a complete sector scan have been loaded, memory 70 is read out in a standard raster scan format for display. Typically, 30 sector scans are produced every second, this being sufficiently rapid to produce a moving image of blood flow and anatomical structure.

Thus, a novel ultrasound diagnostic apparatus has been disclosed. Although a preferred embodiment of the apparatus has been described in some detail, it is to be understood that various changes could be made by persons skilled in the art without departing from the spirit and scope of the invention as defined by the appended claims.

I claim:

1. An ultrasound diagnostic apparatus for mapping blood flow in a body, comprising:
   ultrasonic transmitting means for transmitting a series of temporally spaced ultrasound bursts toward a region where blood flow is to be measured, a number N of said bursts being directed along each of a plurality of beam directions in a scanning plane, where N is an integer from 4 to 8;
   ultrasound receiving means for receiving ultrasound reflected from the blood in response to said ultrasound bursts;
   detecting means for comparing said transmitted ultrasound bursts and said received ultrasound and producing a set of Doppler frequency data $(X_n^k, Y_n^k)$ associated with each of said transmitted bursts in response to said comparison;
   processing means for generating a velocity estimator value $V^k$ representing blood flow velocity at each of several locations, with each of said velocity estimator values along a specific one of said beam directions being generated utilizing said sets of Doppler frequency data $(X_n^k, Y_n^k)$ produced from said number N of ultrasound bursts; and
   display means for displaying an image of said blood flow in response to said velocity estimator value $V^k$ at said several blood locations.

2. The apparatus according to claim 1, wherein said processing means include means for generating said velocity estimator value $V^k$ according to the equation:

$$N = 5 = + |(X_0^k S_0 - Y_0^k T_0 + X_1^k S_1 - Y_1^k T_1 + X_2^k S_2 -$$
$$Y_2^k T_2 + X_3^k S_3 - Y_3^k T_3 + X_4^k S_4 - Y_4^k T_4)| +$$
$$|(X_0^k T_0 + Y_0^k S_0 + X_1^k T_1 + Y_1^k S_1 + X_2^k T_2 +$$
$$Y_2^k S_2 + X_3^k T_3 + Y_3^k S_3 + X_4^k T_4 + Y_4^k S_4)| -$$
$$|(X_0^k S_0 + Y_0^k T_0 + X_1^k S_1 + Y_1^k T_1 + X_2^k S_2 +$$
$$Y_2^k T_2 + X_3^k S_3 + Y_3^k T_3 + X_4^k S_4 + Y_4^k T_4)| -$$
$$|(X_0^k T_0 - Y_0^k S_0 + X_1^k T_1 - Y_1^k S_1 + X_2^k T_2 -$$

where $N = 5V^k$ is said velocity estimator value, where $X_n^k, Y_n^k$ is a set of said Doppler frequency data, $n$ being any of the integers 0, 1, 2, 3 and 4, and where $S_0 = 1; S_1 = -4; S_2 = 6; S_3 = -4; S_4 = 2; T_0 = -2; T_1 = 4; T_2 = 0; T_3 = -4;$ and $T_4 = 2$.
where $N = 5$ is said velocity estimator value, where $X_n^k, Y_n^k$ is a set of said Doppler frequency data, n being any of the integers 0, 1, 2, 3 and 4, and where $S_0 = 1; S_1 = -4; S_2 = 6; S_3 = -4; S_4 = 2; T_0 = -2; T_1 = 4; T_2 = 0; T_3 = -4;$ and $T_4 = 2$.

3. The apparatus according to claim 1, wherein said display means includes a B-scan imaging device.

4. The apparatus according to claim 3, wherein said transmitting means comprises a phased array ultrasonic probe.

5. The apparatus according to claim 1, comprising means for producing a colored image of blood flow, in which image blood flow away from said ultrasonic transmitting means is shown in one color and in which blood flow toward said ultrasonic transmitting means is shown in another color.

6. The apparatus according to claim 1, wherein said processor means comprises a memory and an adder for calculating said velocity estimator value $V^k$ from said set of data $(X_n^k, Y_n^k)$.

7. A method of producing a two-dimensional flow image of a region under investigation using ultrasound, comprising the steps of:
  establishing a predetermined number of directions along which ultrasound is to be propagated, which directions traverse the region and all lie in a common surface;
  propagating a timewise-sequential series of at least 4 and at most 8 discrete ultrasound bursts along each of said directions;
  receiving reflected-back echos of said bursts;
  deriving Doppler shift data indicative, for each of a plurality of points along each direction, of blood flow at said points from said bursts and said reflected-back echos; and
  correlating said shift data with a plurality of points on said surface for deriving said image therefrom.

8. The method of claim 7, comprising the step of superimposing a B-scan image over said two-dimensional flow image.

9. The method of claim 7, wherein said common surface is a plane.

* * * * *

UNITED STATES PATENT AND TRADEMARK OFFICE
CERTIFICATE OF CORRECTION

PATENT NO. : 4,612,937

DATED : September 23, 1986

INVENTOR(S) : Miller

It is certified that error appears in the above-identified patent and that said Letters Patent is hereby corrected as shown below:

TITLE PAGE -

FIELD [63] SHOULD READ:

--This is a continuation of application serial number 550,915 filed November 10, 1983 and now abandoned.--

Column 1, after the title the following text should be inserted:

--This is a continuation of application serial number 550,915 filed November 10, 1983, now abandoned.--

Signed and Sealed this

Tenth Day of February, 1987

*Attest:*

DONALD J. QUIGG

*Attesting Officer*     *Commissioner of Patents and Trademarks*